(12) United States Patent
Heuscher et al.

(10) Patent No.: US 7,058,440 B2
(45) Date of Patent: Jun. 6, 2006

(54) DYNAMIC COMPUTED TOMOGRAPHY IMAGING USING POSITIONAL STATE MODELING

(75) Inventors: Dominic J. Heuscher, Aurora, OH (US); Shiying Zhao, Normandy, MO (US); David D. Matthews, Twinsburg, OH (US); Ge Wang, Iowa City, IA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 776 days.

(21) Appl. No.: 10/179,487

(22) Filed: Jun. 25, 2002

(65) Prior Publication Data

US 2003/0007593 A1 Jan. 9, 2003

Related U.S. Application Data

(60) Provisional application No. 60/301,618, filed on Jun. 28, 2001.

(51) Int. Cl.
*A61B 5/05* (2006.01)

(52) U.S. Cl. .................. 600/428; 600/425; 378/21
(58) Field of Classification Search ............... 600/428, 600/413; 378/8, 14, 21, 62
See application file for complete search history.

(56) References Cited

U.S. PATENT DOCUMENTS

| | | | |
|---|---|---|---|
| 5,544,212 A | 8/1996 | Heuscher | 378/15 |
| 6,078,639 A | 6/2000 | Heuscher | 378/15 |
| 6,104,775 A | 8/2000 | Tuy | 378/4 |
| 6,154,516 A | 11/2000 | Heuscher | 378/15 |
| 6,233,478 B1 * | 5/2001 | Liu | 600/428 |
| 6,252,926 B1 * | 6/2001 | Flohr et al. | 378/15 |
| 6,307,910 B1 * | 10/2001 | Acharya et al. | 378/4 |
| 6,381,487 B1 * | 4/2002 | Flohr et al. | 600/425 |
| 6,504,893 B1 * | 1/2003 | Flohr et al. | 378/8 |
| 6,510,337 B1 | 1/2003 | Heuscher | 600/428 |
| 6,535,570 B1 * | 3/2003 | Stergiopoulos et al. | 378/8 |
| 6,539,074 B1 * | 3/2003 | Yavuz et al. | 378/4 |
| 6,560,309 B1 * | 5/2003 | Becker et al. | 378/8 |
| 6,639,965 B1 * | 10/2003 | Hsieh et al. | 378/8 |
| 6,801,800 B1 * | 10/2004 | Miyazaki et al. | 600/410 |
| 6,879,655 B1 * | 4/2005 | Proksa | 378/4 |

(Continued)

FOREIGN PATENT DOCUMENTS

WO   WO01/43642 A2   6/2001

OTHER PUBLICATIONS

Wang, et al. "A Knowledge-Based Cone-Beam X-Ray CT Algorithm for Dynamic Cardiac Imaging", Sub. to Med. Physics May 30, 2001; 27 pp.

(Continued)

*Primary Examiner*—Brian L. Casler
*Assistant Examiner*—Jennifer Horwat
(74) *Attorney, Agent, or Firm*—Fay Sharpe, Fagan, Minnich & McKee

(57) ABSTRACT

An apparatus for computed tomography (CT) imaging of a cyclically moving organ includes a positional state monitor (24, 40) that monitors a positional state of the cyclically moving organ such as the heart. A cone-beam CT scanner (10) acquires image data at least within a plurality of time windows. Each time window is centered about an occurrence of a selected positional state of the organ. A window analyzer (38) selects a data segment within each time window such that the data segments combine to form a complete data set covering a selected angular range. A reconstruction processor (44) reconstructs the selected data segments into an image representation.

25 Claims, 13 Drawing Sheets

U.S. PATENT DOCUMENTS

2002/0118790 A1* 8/2002 Pan et al. .................. 378/8
2002/0136350 A1* 9/2002 Pan et al. .................. 378/8

OTHER PUBLICATIONS

Wang, et al. "A Knowledge-Based Cone-Beam X-Ray CT Algorithm for Dynamic Cardiac Imaging", Sub. to Med. Physics Sep. 26, 2001; 28 pp.

Wang, et al. "A General Cone-Beam Reconstruction Algorithm", IEEE Trans. on Med. Imaging, vol. 12, No. 3, Sep. 1993, pp. 486-496.

Wang, et al. "Half-Scan Cone-Beam X-Ray Microtomography Formula", Scanning vol. 16, 216-220 (1994).

Bruder, et al., "Segmented Cardiac Volume Reconstruction—A Novel Reconstruction Scheme for Multislice Cardiac Spiral CT", The Sixth Int'l Meeting on Fully Three-Dimensional Image Reconstruction in Radiology & Nuclear Medicine, pp. 161-163.

Moore, et al., "Prospectively Gated Cardiac Computed Tomography", Med. Phys. 10(6), Nov./Dec. 1983 pp. 846-855 XP000996824.

Deng, et al., "Simultaneous Use of Two Ultrasound Scanners For Motion-Gated Three-Dimensional Fetal Echocardiography", Ultrasound in Med. & Biol., V. 26, N. 6, pp. 1021-1032, 2000 XP004295636.

DuMurcia, et al., "Spatio-Temporally Regularized Reconstruction of Gated Spect Myocardial Image Sequences", Proceed. of Int'l Conf. on Image Processing (ICIP) IEEE V. 1, Sep. 16, 1996 pp. 721-724 XP010202759.

Kachelreiss, et al. "ECG-correlated Image Reconstruction from Sub Second Multi-Slice Spiral Scans of the Heart", Med. Phys. 27(8) Aug. 2000, pp. 1881-1992.

Tuy, et al. "3D Image Reconstruction for Helical Partial Cone Beam Scanners" Int'l. Meeting on Fully Three-Dimensional Image Reconstruction in Radiology and Nuclear Medicine, 1999, Proc. of the $5^{th}$ Int'l Conf. on Fully 3D Reconstruction.

Taguchi, et al. "High Temporal Resolution For Multislice Helical Computed Tomography", Med. Phys. vol. 27(2000) pp. 861-872.

Yan, et al., "Cone-Beam Tomography with Circular, Elliptical and Spiral Orbits", Phys. in Med. & Biology, vol. 37(1992) pp. 493-506.

Kudo, et al. "Performance of Quasi-Exact Cone-Beam Filtered Backprojection Algorithm for Axially Truncated Helical Data," IEEE Trans. on Nuclear Science, 46(1999) pp. 608-617.

* cited by examiner

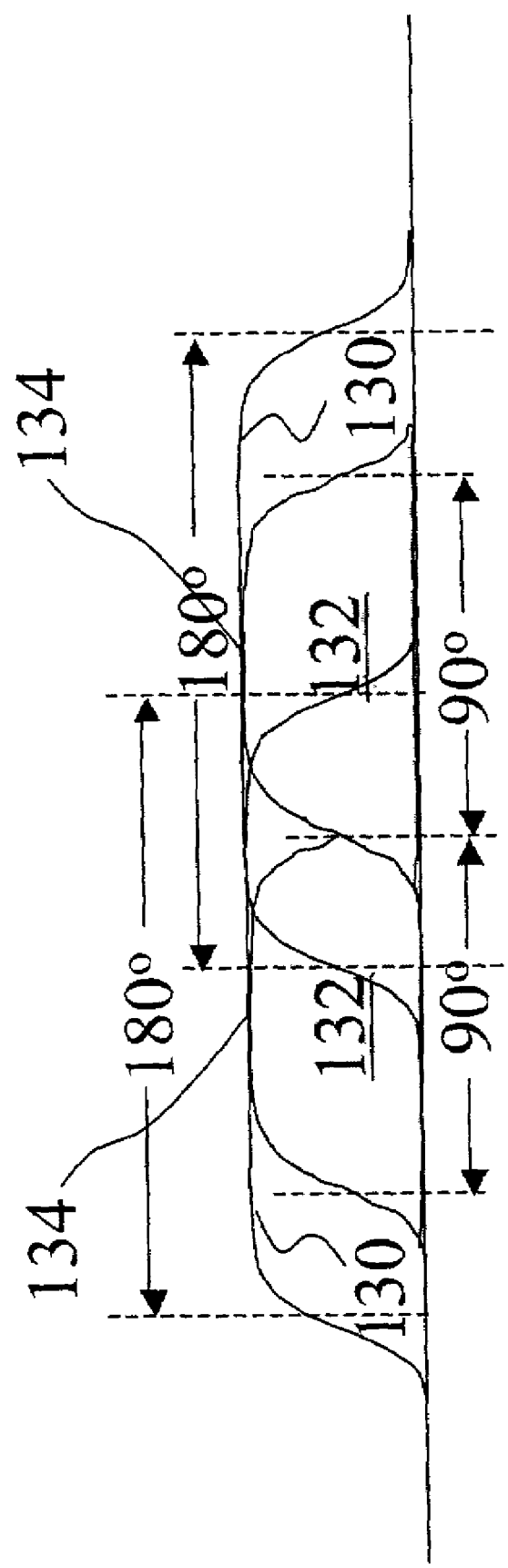

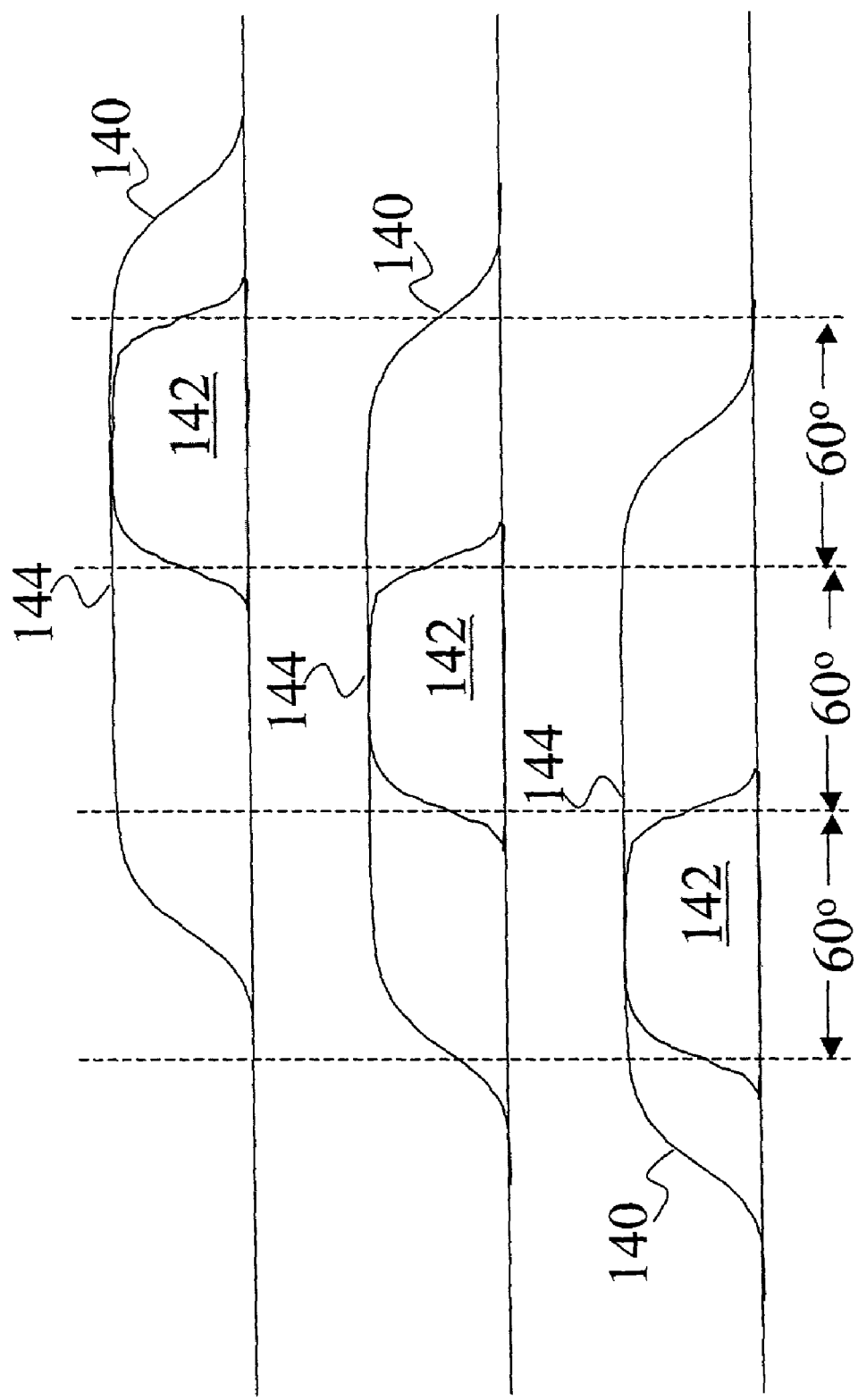

DYNAMIC COMPUTED TOMOGRAPHY IMAGING USING POSITIONAL STATE MODELING

This application claims the benefit of U.S. Provisional Application No. 60/301,618, filed Jun. 28, 2001.

BACKGROUND OF THE INVENTION

The present invention relates to the medical imaging arts. It particularly relates to dynamic volumetric cardiac imaging using computed tomography (CT), and will be described with particular reference thereto. However, the invention will also find application in conjunction with the dynamic volumetric imaging of other non-stationary organs, such as the lungs, in conjunction with time evolution studies, and in conjunction with other imaging techniques and modalities.

It is well known that cardiac diseases are a leading health problem in the United States at the present time. In spite of this prevalence, however, medical diagnosis of cardiac diseases is inconsistent. More than half of the individuals who die of a coronary attack do not exhibit previously recorded symptoms. Hence, there is a need for improved screening and accuracy in the diagnosis of coronary problems.

Medical imaging techniques can image and monitor selected heart functions, such as blood flow or cardiac muscle motion, in real time and without disturbing the heart activity. These techniques are commonly used in diagnosing and monitoring cardiac diseases. However, the existing cardiac imaging modalities, including cardiac angiography, ultrasound, magnetic resonance imaging (MRI), and various forms of computed tomography (CT), are not fully satisfactory. Cardiac angiography is an invasive technique. Ultrasound suffers from poor image quality. MRI typically does not detect calcification, and is subject to various artifacts.

Recent improvements in the speed and resolution of spiral/helical cone-beam and multi-slice CT imaging scanners have led to increased interest in dynamic volumetric CT imaging. Typically, dynamic volumetric cardiac CT imaging includes synchronization with the cardiac cycle using an electrocardiograph (ECG) in a technique known as ECG gating. In prospective ECG gating, detection of a selected ECG waveform or other trigger event controls initiation of CT imaging. In retrospective ECG gating, both the ECG signal and simultaneously acquired CT imaging data are stored in a memory, and the CT image reconstruction is subsequently performed with reference to timing information contained in the stored ECG signal. In a usual approach, ECG-gated cardiac CT imaging data is acquired around a selected cardiac phase of the cardiac cycle, where the cardiac phase is defined as a temporal position within the cardiac cycle.

However, cardiac CT imaging, including cone-beam CT imaging, suffers from motion blurring due to the relatively long CT image scan times needed to acquire projection data with at least 180° of angular coverage. This large angular coverage is typically used to ensure adequate sampling to reconstruct the entire field of view. Obtaining this angular data range involves imaging over a substantial portion of the cardiac cycle.

A typical modern high-speed CT scanner operates at about 120 x-ray source revolutions per minute corresponding to 500 milliseconds per revolution, so that a 180° angular scan takes about 250 milliseconds. A typical heart pulse rate of 70 beats per minute corresponds to a cardiac cycle period of 857 milliseconds. Hence, the imaging occurs, not at a single well-defined cardiac cycle phase, but rather over a substantial fraction of an entire cardiac cycle, i.e. over almost 30% of the cardiac cycle in the exemplary case. The motion of the cardiac muscle as data is acquired over this extended time causes motion-related image blurring. The high pulse rates often characteristic of patients with coronary diseases further increases motion image blurring.

To improve temporal resolution, it is known to acquire projection image data over two or more cardiac cycles while simultaneously monitoring the cardiac cycle using ECG gating. Data at the selected cardiac phase is extracted and combined from the two or more cardiac cycles based on the cardiac phase determined by the ECG. By distributing the imaging over two or more cardiac cycles, the data acquisition period within each cycle is shortened, which improves temporal resolution with respect to the cardiac cycling because a smaller portion of the cardiac cycle is sampled.

As more cardiac cycles are sampled, the data acquisition period within each cycle becomes shorter and the temporal resolution with respect to the cardiac cycling improves. However, collecting imaging data over more cycles can introduce other artifacts. First, patient motion is more likely to occur as the number of sampled cardiac cycles (and hence the total imaging time for a reconstructed view) increases.

Additional artifacts can be introduced by variations in the cardiac cycle period (i.e., the pulse rate) between the several sampled cardiac cycles. Data is acquired at a cardiac phase corresponding to a selected temporal position within the cardiac cycle. It is known in the art to use a cardiac phase defined as a percentage temporal position within the cardiac cycle to account for changes in the cardiac cycle period. However, the various physiological portions of the cardiac cycle, e.g. the systolic and diastolic portions and physiological events therein, do not linearly scale with changes in the cardiac cycle period, and so using a percentage temporal position does not fully compensate for changes in the pulse rate.

Third, image artifacts can be introduced in helical cone-beam CT due to an introduction of potential inconsistencies in the angular deviation in the Z-direction (i.e., the cone angle) at segment boundaries. In helical cone-beam CT, the x-ray beam diverges in the Z-direction and the patient is linearly moved or scanned in the Z-direction during the imaging. The cone angle of the x-rays in the Z-direction varies continuously during continuous helical scanning. However, when discontinuous data segments are combined to form a complete data set, there can be inconsistencies in the cone angle at the data segment boundaries. Although the data can still be combined to produce a complete data set of 180° or greater angular coverage, potential cone angle inconsistencies in the Z-direction at the data segment boundaries can produce artifacts in the reconstructed image.

Another issue that arises in ECG-gated CT performed over several cardiac cycles is coordinating between the angular rotation of the x-ray source and the cardiac cycle such that data obtained from successive cardiac cycles is complementary rather than partially redundant. The data preferably combines to generate a continuous data set over the desired angular coverage, e.g. 180°; however, this is not always the case.

Two undesirable limiting cases exemplify the coordination issue. In the first limiting case, the cardiac cycle period is an integer multiple of the gantry rotation period, i.e. $T_{cc} = nT_{rot}$ where n is an integer, $T_{rot}$ is the gantry rotation period, and $T_{cc}$ is the cardiac cycle period. Under this condition, for any temporal window triggered by a selected cardiac phase the same angular span of CT projection data will be acquired in successive cardiac cycles. This data is not complementary and does not provide increased angular coverage versus the data acquired during a single cardiac cycle.

In the second limiting case, the period relationship is $T_{cc}=(n+\frac{1}{2})T_{rot}$. The gantry angles in this case will be 180° apart at any particular selected cardiac phase in any two successive cardiac cycles. Redundant data is collected in alternate cardiac cycles. The two acquired data sets will be angularly displaced by 180°, with a significant angular gap between the two data sets, which produces image artifacts. In cardiac ECG-gated CT, angular data portions are preferably combined into a contiguous but substantially non-overlapping data set.

In one previous approach to this problem, the cardiac period is estimated using an ECG, and the CT scanning rate is synchronized with the estimated cardiac cycle. However, this method is susceptible to problems due to changes in the cardiac cycle period between the calibration and the imaging, or during the imaging. Some variation in the cardiac cycling is to be expected since the examined patient is usually in an anxious state and is being asked to hold his or her breath over the course of the image acquisition. Also, patients having coronary disease often suffer from heart arrhythmia wherein the cardiac cycle is unpredictably non-periodic. Another drawback to this method is that the CT scanning rate is reduced to correspond with the heart rate. Hence, the CT apparatus is typically being operated below its rated capabilities (e.g., 120 rpm) when using this method.

The present invention contemplates an improved method and apparatus for imaging dynamically moving organs which overcomes the aforementioned limitations and others.

SUMMARY OF THE INVENTION

According to one aspect of the invention, a method is provided for acquiring diagnostic imaging data of a dynamically moving organ. A positional state of the organ motion is monitored as a function of time. Time windows are selected and arranged about occurrences of a selected positional state. Imaging data of the dynamically moving organ is acquired at least during the time windows. Portions of the imaging data acquired during the time windows are combined to form a complete image data set. An image representation is reconstructed from the complete image data set.

According to another aspect of the invention, an apparatus is disclosed for computed tomography (CT) imaging of a cyclically moving organ. A positional state monitor monitors a positional state of the cyclically moving organ. A cone-beam CT scanner acquires image data at least within a plurality of time windows. Each time window is centered about an occurrence of a selected positional state of the organ. A window analyzer selects a data segment within each time window such that the data segments combine to form a complete data set covering a selected angular range. A reconstruction processor reconstructs the selected data segments into an image representation.

According to yet another aspect of the invention, an apparatus is disclosed for acquiring volumetric medical imaging data of a dynamically moving organ. A means is provided for monitoring an anatomical state of the organ motion cycling. A means is provided for determining time windows centered on occurrences of substantially similar states of organ motion cycle. A means is provided for acquiring imaging data at least during the time windows. A means is provided for combining portions of the imaging data acquired during the time windows to form a complete image data set. A means is provided for reconstructing an image representation from the complete image data set.

One advantage of the present invention is that it improves temporal and spatial resolution of images of moving anatomy.

Another advantage of the present invention is that it identifies a plurality of data acquisition windows in each cardiac cycle.

Yet another advantage of the present invention resides in improved accuracy of diagnostic information.

Still yet another advantage of the present invention is that it selects and combines CT image data to optimally provide a selected angular coverage.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

FIG. 6C shows a schematic representation of selection of data portions for reconstruction using cardiac segmented gating over two cardiac cycles where the two time windows are optimally located.

FIG. 7 shows a schematic representation of selection of data portions for reconstruction using cardiac segmented gating over three cardiac cycles.

DETAILED DESCRIPTION OF THE PREFERRED EMBODIMENTS

Figure 1:
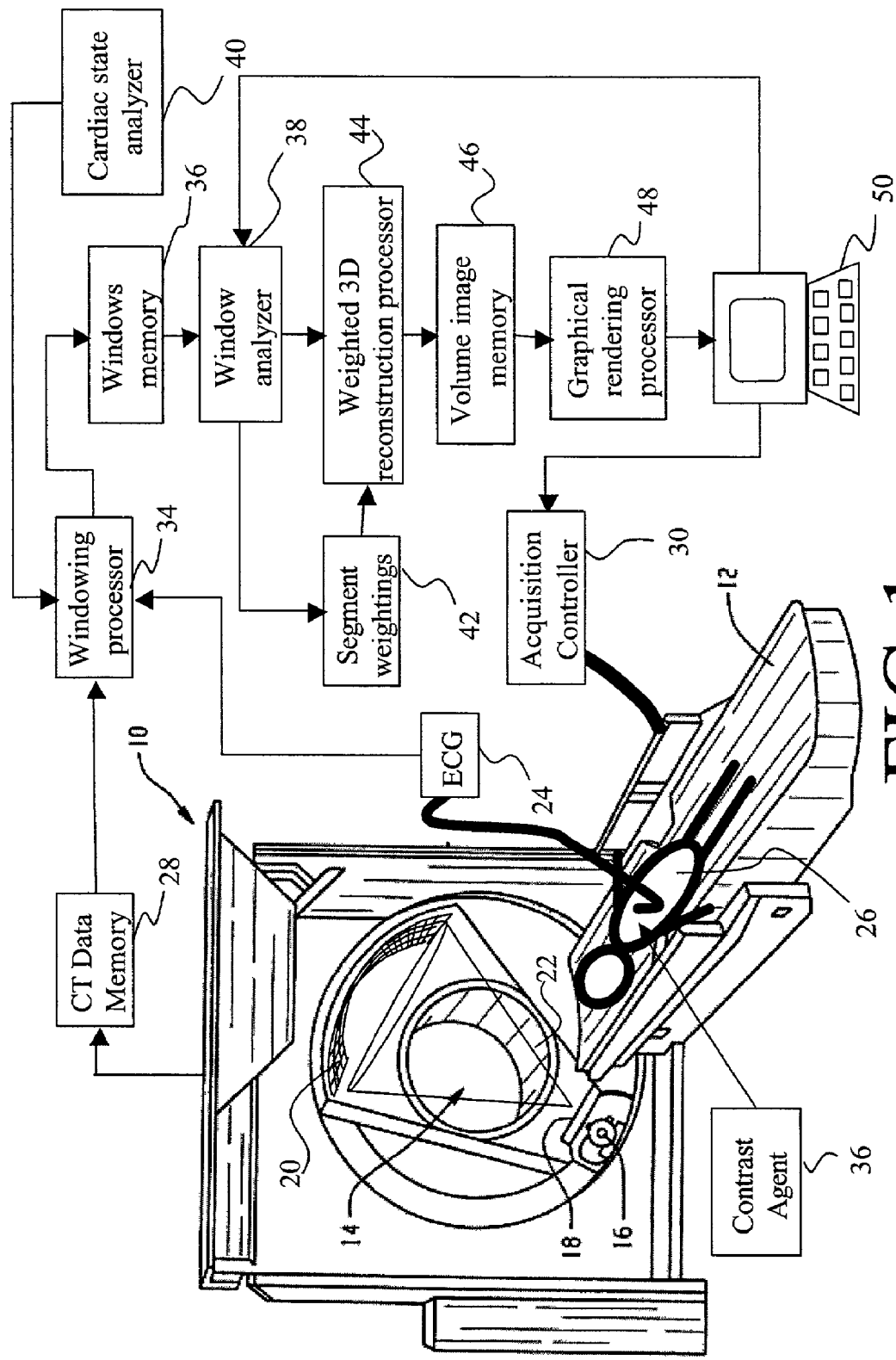
FIG. 1 schematically shows an exemplary cone-beam CT imaging system that suitably practices an embodiment of the invention.

With reference to FIG. 1, an exemplary cone-beam computed tomography (CT) scanner 10 includes a subject support 12 such as a patient couch which is linearly movable inside an examination region 14. An x-ray tube assembly 16 mounted on a rotating gantry projects x-rays through the examination region 14. A collimator 18 collimates the radiation in two dimensions. In the exemplary CT scanner 10, a two-dimensional x-ray detector array 20 is disposed on the rotating gantry across the examination region from the x-ray tube. In an alternative embodiment (not shown), the detector array includes an array of two-dimensional detector rings mounted in a stationary fashion around the rotating gantry.

In the exemplary cone-beam CT scanner 10, the x-ray tube assembly 16 cooperates with the collimator 18 to produce a conical or wedge-shaped beam 22 which diverges conically as it passes through the examination region 14. The cone beam 22 substantially covers the detector array 20, which in a suitable embodiment includes sixteen rows of 1–10 mm detectors. It will be recognized that in the cone-beam geometry the x-ray paths to the various elements of the detector array 20 are not generally parallel. In another embodiment (not shown), a plurality of substantially parallel fan beams of radiation are generated, with each parallel beam detected by a corresponding row or rows of detectors. In a common implementation of this embodiment, four detector rows are employed. More detector rows can be accommodated by using an x-ray tube with a multiple-anode assembly.

Regardless of the detailed geometry of the x-ray beam 22 and the detector array 20, the x-ray detectors 20 operate in known ways to convert x-rays 22 that have traversed the examination region 14 into electrical signals indicative of x-ray absorption between the x-ray tube 16 and the detectors 20. For cardiac CT imaging, a patient 26 is positioned via the patient support 12 with the patient's heart within the examination region 14 such that the x-ray beam 22 passes through the heart and associated vasculature.

An electrocardiogram (ECG) 24 monitors the cardiac phase of the patient's 26 heart. A cardiac phase is a temporal position within the cardiac cycle, and is preferably defined relative to the cardiac cycle period, e.g. as a percentage position within the cardiac cycle, to approximately compensate for variations in the cardiac cycle period. Such variations in the cardiac cycle period, i.e. the patient's pulse rate, can occur due to stress resulting from the CT examination, medical conditions such as heart arrhythmia, or the like.

The x-ray absorption signals, along with information on the angular position of the rotating gantry and the longitudinal position of the patient support 12, are communicated to a CT data memory 28. An acquisition controller 30 communicates with the CT scanner 10 to control CT scanning of the patient 26. The CT scanner 10 acquires projection data with a plurality of viewing angles by rotating the gantry that carries the x-ray source 16. Scanning in the z-direction is performed by moving the patient 26 linearly via the patient couch 12. In spiral or helical CT imaging, the patient couch 12 advances simultaneously with the gantry rotation such that the data acquisition occurs using a spiral geometry respective to the patient 26. Spiral/helical CT has the advantage of continuous and rapid data acquisition.

The acquired CT projection data is stored in the CT data memory 28 with the corresponding cardiac phase, angular position of the cone and the longitudinal position along the patient. A windowing processor 34 identifies a window of contiguous projection data sets centered on one or more user-selected cardiac phases in one or more cardiac cycles. The windows are loaded into a series of window memories or buffers 36. A window analyzer 38 selects data segments or sets which are optimally centered within their window and which taken together define a complete data set for reconstruction. The window analyzer 38 preferably associates a segment weighting 42 with each data segment. Suitable segment weightings 42 reduce the amplitude of data near the segment boundaries to suppress artifacts due to inconsistencies at the segment boundaries, such as inconsistencies in the cone angle in the Z-direction.

Preferably, the window processor 34 accesses a cardiac state analyzer or memory 40 which identifies one or more cardiac phases in which the organ of interest, e.g. the heart, is in a selected anatomical or positional state. As used herein, a positional state refers to a selected position of the moving organ of interest, e.g. the heart. A moving organ can move in an oscillatory or back-and-forth translational motion in which a selected positional state occurs twice within a single period of the organ motion. The moving organ can instead move in a rotational orbit, in which a selected positional state typically occurs only once per period of organ motion. As used herein, positional state can also refer to a dilation/contraction motion of the organ about a central position. In such a dilation/contraction motion, the organ may or may not translate positionally, and a selected state can occur one or more times within a single organ motion period. Furthermore, the organ motion can be a combination of motions and/or contraction/dilation.

The cardiac state, i.e. the selected anatomical or positional configuration of the heart or other cyclically varying region of interest, can be extracted using a state-phase model such as a cardiac state-cardiac phase model which relates a temporally varying diagnostic signal measured during the CT data acquisition with the anatomical position of the organ of interest. Alternatively, the state can be directly measured during the CT imaging, for example using an ultrasonic imaging performed simultaneously with the CT data acquisition. The state can also be extracted from the CT imaging data itself using an iterative reconstruction in which successive reconstruction iterations more precisely define the state of the organ of interest, which is in turn used to select data for the next reconstruction iteration which more closely correlates with the state of interest.

Anatomical or positional state synchronization recognizes that the important aspect of synchronization for a dynamically moving organ or other region of interest is that the imaged region of interest have a relatively stable and stationary spatial configuration throughout the data acquisition, which need not be temporally contiguous. The positional state concept can be used to select CT imaging data portions that closely correspond with the state of interest. Alternatively or in combination, knowledge of the organ's positional state can be used to select a relatively stationary state of the organ at which to perform the CT imaging.

Optionally, the cardiac state analyzer 40 includes a correction, parameter, or other adjustment that compensates for variations in the cardiac cycle with the cardiac cycle period or with other parameters such as patient age, physical condition, or the like. One suitable compensation adjustment is described in Heuscher. et al., U.S. Pat. No. 6,510,337, entitled "Multi-Phase Cardiac Imager".

The selected CT data segments are input to a reconstruction processor 44 together with the corresponding segment weightings 42. The reconstruction processor 44 reconstructs a three-dimensional image representation of the region of interest at the selected cardiac state. The reconstructed image is stored in a volume image memory 46. The reconstruction processor 44 operates on a complete data set constructed from the data segments along with the corresponding segment weightings 42. Preferably, the complete data set is weighted using a cosinusoidal weighting or other selected weighting. The selected weighting reduces the contribution of data at the boundaries of the complete data set to reduce potential artifacts due to inconsistencies at the boundaries.

One suitable three-dimensional reconstruction is a modified wedge-rebinned reconstruction such as is described by U.S. Pat. No. 6,104,775 issued to Tuy. Another suitable reconstruction is a three-dimensional modified Feldkamp-type cone-beam reconstruction such as is described by G. Wang et al., "A general conebeam reconstruction algorithm", IEEE Transactions on Medical Imaging, MI-12 (1993), pp. 486–496. Other three-dimensional reconstruction techniques can also be employed in the reconstruction processor 44.

The reconstructed image is advantageously processed by a graphical rendering processor 48 and displayed on a user interface 50. In a typical CT apparatus, the user interface 50 also allows a clinician, diagnostician, or other user to select, create, modify, or execute an appropriate scanning program that directs the acquisition controller 30.

Those skilled in the art will be able to make further modifications of the system of FIG. 1 to suit particular applications. For example, the user interface 50 can include other components, such as printers, network connections, storage units, and the like (not shown), to facilitate efficient manipulating of the CT scanner 10.

Figure 2:
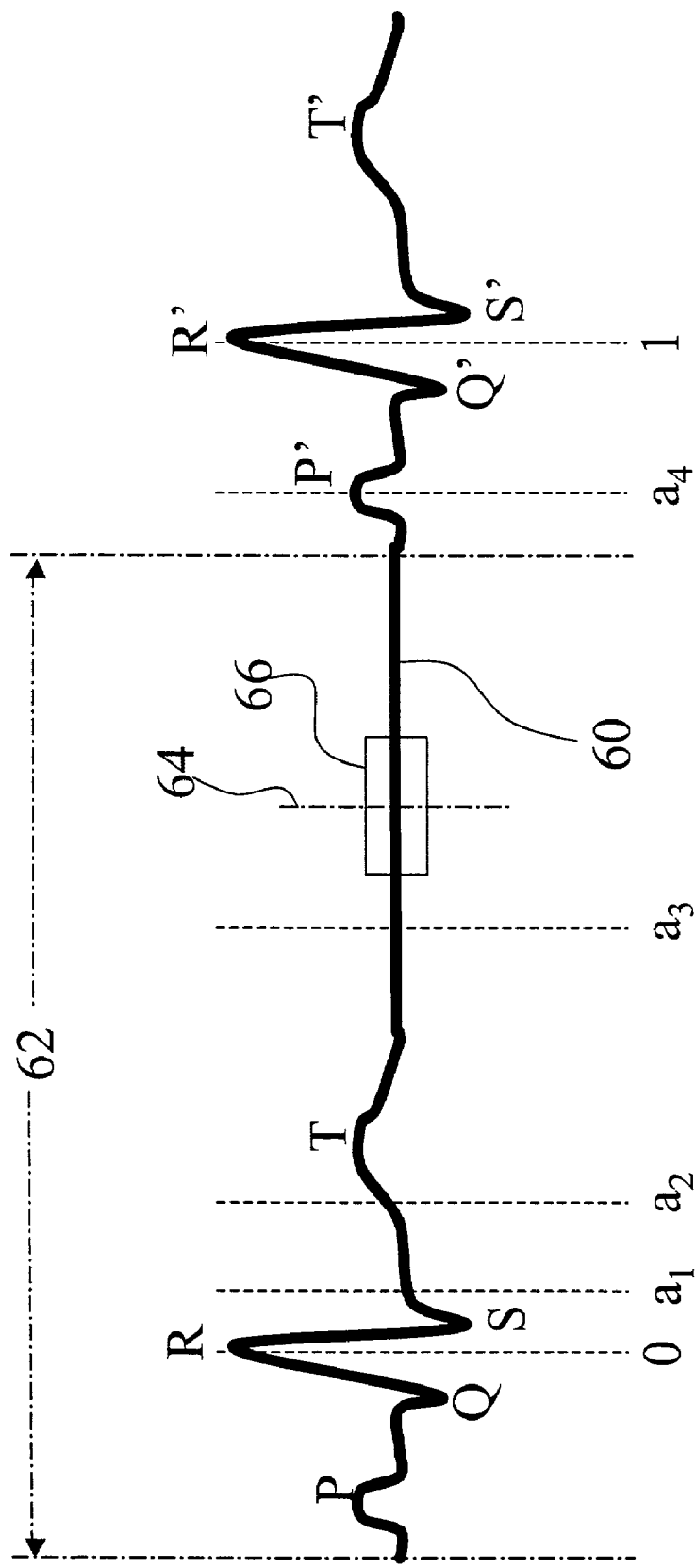
FIG. 2 shows an exemplary schematic electrocardiograph recording for associating a cardiac state with a cardiac phase.

With continuing reference to FIG. 1 and with further reference to FIG. 2, a schematically represented ECG signal 60 corresponds to electrical potentials generated by the heart on the surface of the body and recorded using the ECG 24. The ECG signal 60 typically includes several identifiable wave-forms which can be associated with motion of the cardiac organ or portions thereof. The most prominent wave-forms are referred to in the art as P, Q, R, S, and T waves indicated in FIG. 2. The P wave is caused by the spread of depolarization through the atria, followed by atrial contraction. Shortly after the P wave, the Q, R, S wave pattern appears due to depolarization of the ventricles, which initiates ventricular contraction. The T wave indicates repolarization of the ventricles, and occurs slightly before relaxation.

The ECG signal 60 is quasi-periodic with a cardiac cycle 62, represented in FIG. 2 by a cycle repetition including wave-forms P', Q', R', S', and T' corresponding to wave-forms P, Q, R, S, and T. The cardiac cycle repeats in a quasi-periodic manner which however varies from perfect periodicity due to influences such as physical exertion, emotional stress, the presence of certain drugs, medical conditions such as heart arrhythmia, and the like.

Those skilled in the art know that in addition to a varying cardiac cycle period, e.g. pulse rate, the anatomical or positional variation of the heart during the cardiac cycle can vary in a non-linear fashion with the cardiac cycle period. Additionally, the positional variation of the heart within the cardiac cycle can vary significantly from patient to patient, and especially between patients of different age groups or between patients having medical conditions such as coronary disease. A selected cardiac phase 64 is identified as a selected temporal point within the cardiac cycle 62 which corresponds to a selected positional cardiac state as indicated by the cardiac state analyzer 40.

Although cardiac cycle monitoring using an ECG is described herein, other methods for monitoring the cardiac cycle and detecting a selected cardiac state can also be used. For example, a phonocardiogram (not shown) detects acoustical signals associated with the heart cycling, and can be used to monitor the cardiac cycle and detect a cardiac phase corresponding to a selected positional state of the heart. Alternatively, the cardiac positional state can be directly measured, e.g. using concurrent ultrasound imaging, or can be extracted from the CT data itself by iterative reconstruction.

Retrospective cardiac gating involves synchronizing the CT data with cardiac phase after data acquisition. In contrast, synchronization of the data acquisition with a selected cardiac phase as the CT data is acquired is known in the art as prospective cardiac gating. Prospective gating is particularly useful in dose modulation CT imaging techniques, in which the x-ray beam intensity is applied at full strength only during selected data acquisition periods, and is lowered or shuttered at other times to reduce the patient's total x-ray radiation exposure. Although retrospective cardiac gating is exemplarily described herein, those skilled in the art can readily modify the presently described inventive method and apparatus embodiments to employ prospective gating.

With continuing reference to FIG. 2, it will be appreciated that synchronization with the selected cardiac phase 64 results in a single window of opportunity 66 for CT data collection occurring per cardiac cycle. The window of opportunity 66 includes a selected temporal range about an occurrence of the selected cardiac phase 64. Increasing the width of the window 66 typically reduces the image quality through cardiac motion blurring. However, 180° plus fan angle of angular CT data is typically desired for optimum performance of most image reconstruction techniques. For a 120 rpm gantry rotation, 180° of CT projection data corresponds to 250 milliseconds of data acquisition. At a heart pulse rate of 60 beats per minute this corresponds to data collection over 25% of the cardiac cycle. The percentage increases for higher pulse rates, which often occur in patients having heart problems, or for reconstruction algorithms requiring greater than 180° of CT projection data coverage.

One advantage of synchronization with a cardiac state, rather than a cardiac phase, is that if the cardiac motion of interest is oscillatory or a stationary expansion/contraction, more than one window of opportunity is optionally identified during each cardiac cycle. For example, a heart chamber (e.g., left or right atrium or ventricle) can be modeled as a contracting/dilating organ for which two windows can be defined in each cardiac cycle during which the selected heart chamber lies within a selected physical size range—one window occurring during contraction of the heart chamber, and another window occurring during expansion or dilation of the heart chamber. For a state so defined, the cardiac state analyzer 40 includes a lookup table or empirical formula that provides the heart chamber volume as a function of the cardiac phase.

Considering the left ventricle, within a single cardiac cycle more than one non-contiguous cardiac phase can correspond to a single cardiac state defined with respect to the left ventricle volume. The left ventricle contracts and expands during each cardiac cycle, and so there are two cardiac phases during each cardiac cycle at which the left ventricle has a particular intermediate volume. Given appropriate knowledge in the form of a cardiac state-cardiac phase model in which the cardiac state is defined as the left ventricular volume, the cardiac state analyzer 40 (FIG. 1) identifies these two cardiac phases and the CT projection data acquisition (prospective cardiac gating) or data selection (retrospective cardiac gating) are coordinated with these two cardiac phases.

Alternatively, the cardiac state is defined as an anatomical or physical signal, that corresponds for example to the configuration of the left ventricle, and which signal can be directly measured to enable the coordination. For instance, ultrasound imaging (not shown) can be used to directly image and estimate the ventricular volume and thus obtain the cardiac state information.

In yet another embodiment, CT imaging is used to construct a cardiac state-cardiac phase model by taking a plurality of images during the cardiac cycle and measuring a selected parameter such as the ventricular volume. It will be recognized that the image quality for these measurements typically does not need to be very high, since a clinical diagnosis is not being extracted. In some instances, the cardiac state can be determined by analyzing one or a small number of projection data sets.

Figure 3:
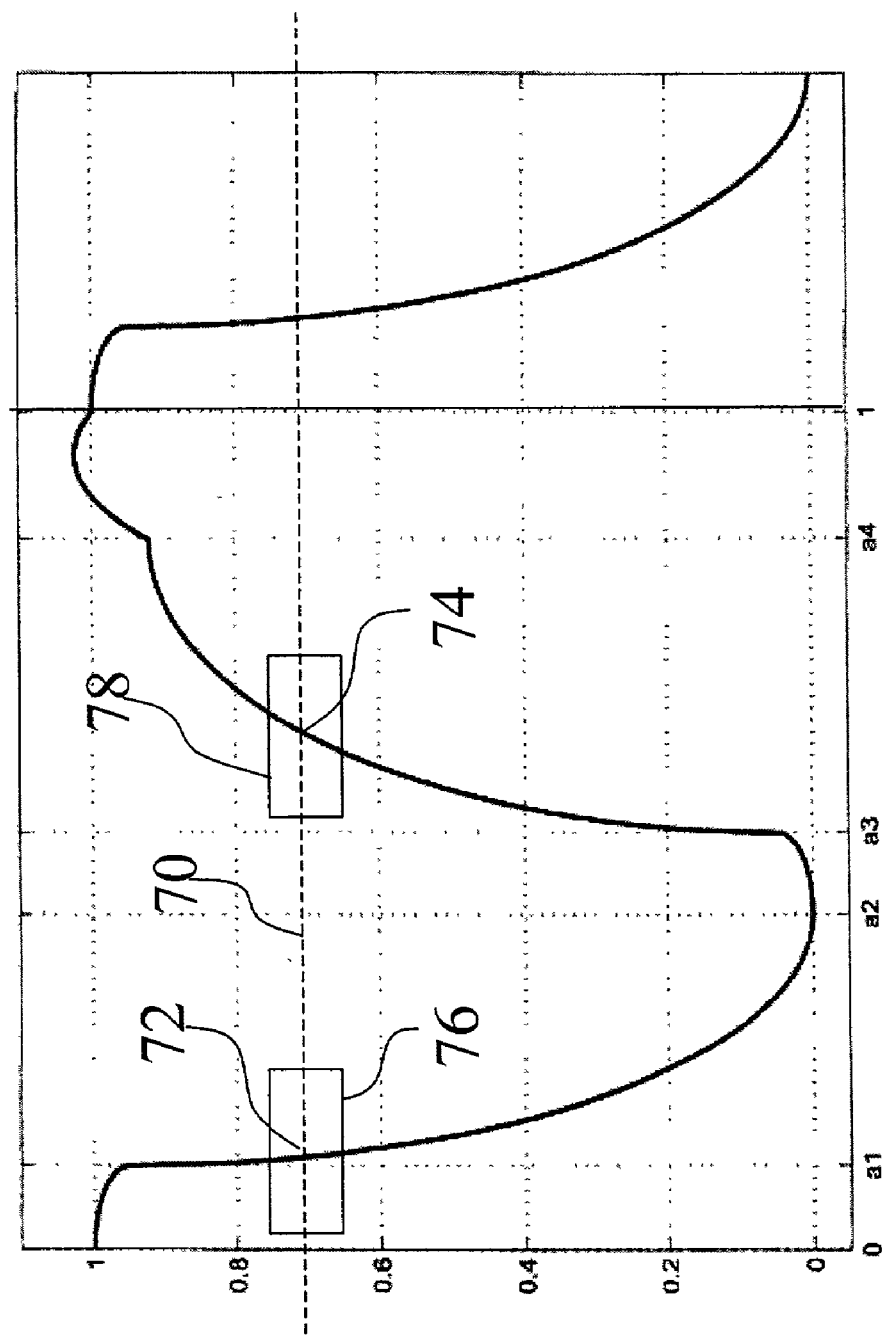
FIG. 3 shows a parametric cardiac state-cardiac phase model relating the left ventricular volume to the cardiac phase.

With continuing reference to FIGS. 1 and 2, and with further reference to FIG. 3, an exemplary parametric functional model for the left ventricular volume positional state as a function of the cardiac phase is described. This model is incorporated into the cardiac state-cardiac phase analyzer 40 of FIG. 1 to implement cardiac state synchronization. The left ventricular volume is defined in the exemplary parametric functional model as:

$$v = f(t) = \begin{cases} f_s(t), & \text{for } 0 \leq t \leq a_3 \\ f_d(t), & \text{for } a_3 \leq t \leq 1 \end{cases}, \quad (1)$$

where $a_3$ is indicated in both FIG. 2 and FIG. 3 and corresponds to the transition point from the systolic cardiac phase to the diastolic cardiac phase, $f_s(t)$ describes the left ventricular volume in the systolic phase during which the left ventricle is contracting, and $f_d(t)$ describes the left ventricular volume in the diastolic phase during which the left ventricle is relaxing and expanding.

The systolic $f_s(t)$ is typically monotonically decreasing (ventricle contracting) while diastolic $f_d(t)$ is typically monotonically increasing (ventricle expanding). A suitable parametric model for the left ventricular volume expressed using piecewise-integrated functional segments as:

$$v = f(t) = \begin{cases} g(t; 0, 1, a_1, b_1, 0) & \text{for } 0 \leq t \leq a_1 \\ g(t; a_1, b_1, a_2, b_2, a_3) & \text{for } a_1 \leq t \leq a_2 \\ g(t; a_2, b_2, a_3, b_3, a_3) & \text{for } a_2 \leq t \leq a_3 \\ g(t; a_3, b_3, a_4, b_4, a_4) & \text{for } a_3 \leq t \leq a_4 \\ g(t; a_4, b_4, 1, 1, c) & \text{for } a_4 \leq t \leq 1 \end{cases} \quad (2)$$

$$\text{where } g(t; x_1, y_1, x_2, y_2, c) = \alpha + \beta \sqrt{1 - \left(\frac{t-c}{x_2 - x_1}\right)^2}, \quad (3)$$

$$\alpha = \frac{y_2 \sqrt{(x_2 - c)(x_2 - 2x_1 + c)} - y_1 \sqrt{(x_1 - c)(x_1 - 2x_2 + c)}}{\sqrt{(x_2 - c)(x_2 - 2x_1 + c)} - \sqrt{(x_1 - c)(x_1 - 2x_2 + c)}}, \quad (4)$$

$$\beta = \frac{-(y_2 - y_1)(x_2 - x_1)}{\sqrt{(x_2 - c)(x_2 - 2x_1 + c)} - \sqrt{(x_1 - c)(x_1 - 2x_2 + c)}}, \quad (5)$$

and the cardiac phases $a_1$, $a_2$, $a_3$, $a_4$, and $a_5$ are identified in FIGS. 2 and 3. The parameters in the model of equations (1) through (5) can be estimated from published studies relating the ECG to the left ventricular volume. Alternatively, the parameters can be fitted from actual CT images taken of the patient under examination.

With continuing reference to FIG. 3, a cardiac state 70 defined by a left ventricular volume of 70% of full volume expansion is indicated. There are two cardiac phases 72, 74 for which the selected cardiac state 70 occurs, one 72 in the systolic or contracting portion of the cardiac cycle and the other 74 in the diastolic or relaxing portion of the cardiac cycle. Two corresponding windows of opportunity 76, 78 are available during each cardiac cycle.

Figure 4:
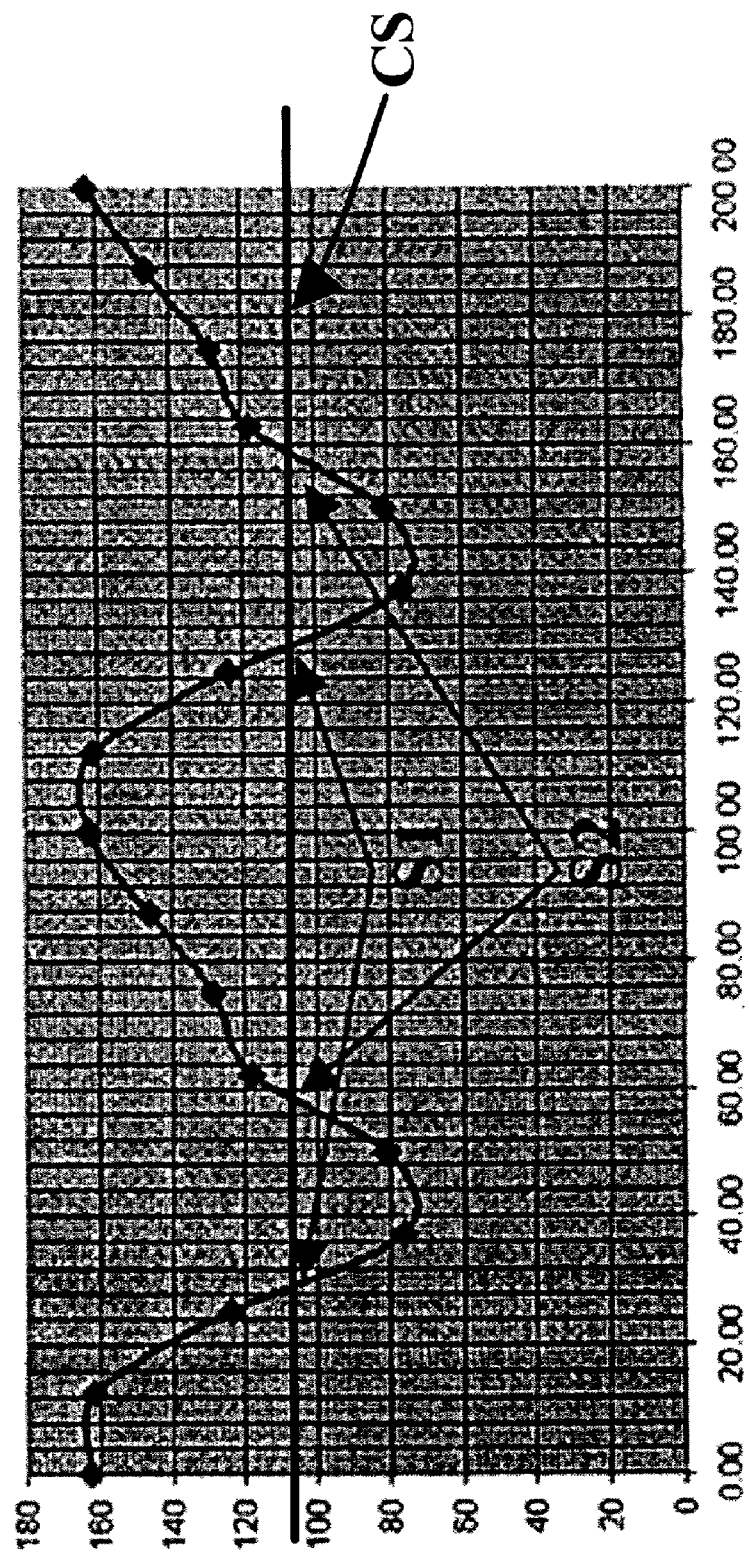
FIG. 4 shows an empirical cardiac state-cardiac phase model relating the left ventricular volume to the cardiac phase.

With reference to FIG. 4, another cardiac state-cardiac phase model using the left ventricular volume as the cardiac state is shown. This model was obtained using cardiac ECG-gated CT imaging, with volume values extrapolated from images represented by filled diamonds (♦). It will be appreciated that since the images used to generate the experimental model of FIG. 4 are not used for clinical diagnosis, but rather are only used to determine the cardiac state-cardiac phase relationship, the image quality need not be optimal. Furthermore, volume measurements are an integrative process which are relatively insensitive to noise and localized image defects. The curve is shown in FIG. 4 repeats over two cardiac cycles, with two cardiac phases S1, S2 indicated which correspond to a single cardiac state CS having a left ventricular volume of about 105 cc.

The assigning of a positional cardiac state in the examples herein as the left ventricular volume is representative only. Those skilled in the art will recognize that the cardiac state can be defined by other cardiac parameters, such as a heart chamber volume other than the left ventricle volume (e.g. an atrial volume), a position of the cardiac muscle during the cardiac cycling, or the like. The selected state preferably relates to the cardiac portion to be imaged (e.g., ventricle, atrium, and et cetera), and is selected based on the available knowledge base relating to the anatomical motion of that cardiac portion during the cardiac cycle, the available diagnostic anatomical or physical measurements, and the like.

Those skilled in the art will further recognize that the state concept is not limited to cardiac CT imaging or to cardiac dynamic volumetric imaging. The state concept is applicable to the imaging of substantially any organ that exhibits quasi-periodic motion or behavior, such as the lungs, major arteries, and the like. Those skilled in the art will still further appreciate that the state concept is not limited to any particular medical imaging modality (e.g., MRI, SPECT, PET, et cetera). For example, the cardiac state-cardiac phase diagram of FIG. 3 or FIG. 4 can be used in conjunction with multiple-echo cardiac gated MRI in which selected k-space lines are acquired during each of the two windows 76, 78 over several cardiac cycles.

Many periodic motions include increasing and decreasing intervals within each period (e.g., expanding and contracting lung volume, increasing and decreasing blood flow in the aorta, and the like), there will be at least two occurrences of a selected intermediate state per period. In these cases, the state concept will typically yield at least a two-fold increase in the total imaging window length in each organ motion cycle. The state concept improves diagnostic imaging for such periodic motions by enabling image data acquisition at a plurality of typically non-contiguous intervals within a single cycle of organ motion.

The state concept provides several benefits for gated cardiac CT. First, it can provide multiple non-contiguous imaging windows in a single cardiac cycle, as described above. Second, it provides improved accuracy in the data selection by better defining the target cardiac phase at which imaging data should be acquired by relating the phase to a positional state of the heart. Third, knowledge of the cardiac state can improve imaging by identifying portions of the cardiac cycle in which the heart (or the portion of the heart being imaged) is substantially stationary.

However, in CT the combined data should be angularly complementary so that the different intervals combine to provide a 180° or other desired angular coverage. Preferably, the projection data combines to form an angularly contiguous but substantially non-overlapping angular range having the desired angular coverage. An identified target cardiac phase which corresponds to a selected cardiac state may not be well-positioned within the rotational cycle of source.

Figure 5:
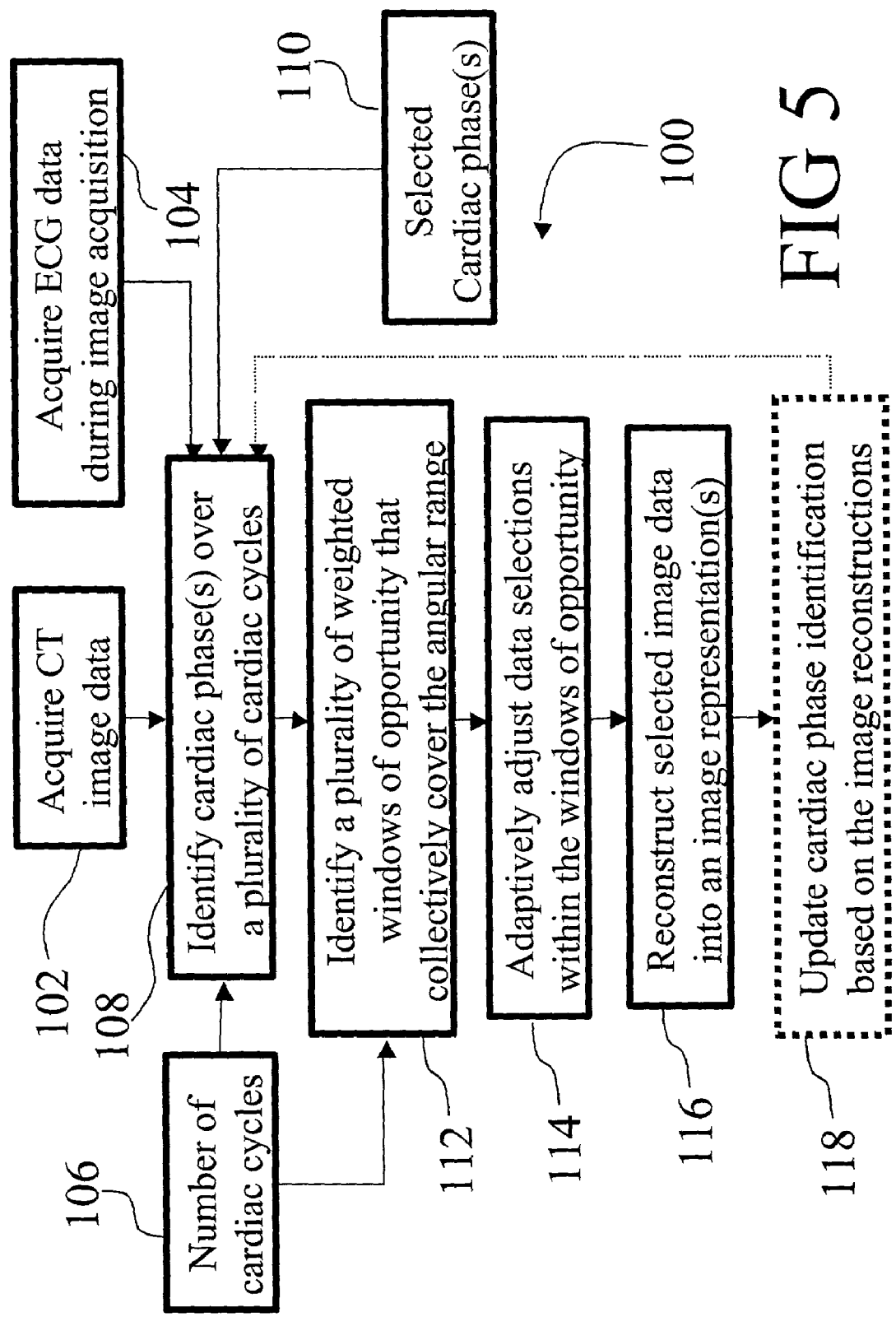
FIG. 5 shows a flow chart of an exemplary method for adaptively selecting and reconstructing CT imaging data corresponding to a selected cardiac phase or phases acquired over one or more cardiac cycles.

With reference to FIG. 5, an exemplary embodiment 100 of a method for data sorting, selection, and reconstruction using retrospectively gated cardiac CT data is described, which suitably combines temporally non-contiguous projection data intervals. With retrospective gating, CT image data acquisition 102 and ECG data acquisition 104 occur simultaneously. In one suitable embodiment, there is no a priori synchronization of the CT scanning (e.g., spiral pitch, gantry rotation rate) and the cardiac cycle as indicated by the ECG.

Alternatively, some approximate synchronization is performed. For example, in segmented gating it may be desirable to verify a priori that the pitch and scan rate are such that each voxel will remain within the x-ray cone beam range for at least a selected number of cardiac cycles 106 over which the image data portions are to be acquired. It can also be desirable, particularly at lower gantry rotation rates, to approximately synchronize the gantry rotation with the cardiac cycle to ensure that the selected cardiac phase is imaged at approximately complementary gantry angles during successive cardiac cycles. However, it is understood that variations in the patient's cardiac cycle make precise a priori synchronization practically unachievable. This is particularly true because the patient 26 is typically in a state of high anxiety responsive to undergoing CT examination, and because the patient 26 is typically suffering from coronary problems, which may include arrhythmic symptoms.

Regardless of whether an initial approximate synchronization is performed, the CT image data acquisition 102 and the ECG data acquisition 104 occur simultaneously. The ECG data is analyzed in a step 108 to identify a number of cardiac cycles corresponding to the selected number of cardiac cycles 106, and to identify a temporal point in each cardiac cycle corresponding to an occurrence of a selected cardiac state 110. Optionally, there are a plurality of selected cardiac phases in each cycle corresponding to the selected cardiac state 110.

A plurality of windows of opportunity are defined 112 centered about the identified occurrences of the selected cardiac state 110. Typically, data from two or more cardiac cycles 106 are combined; however, if there are multiple occurrences of the state in each cardiac cycle, then optionally two or more non-contiguous windows are defined in a single cardiac cycle. The width of each window of opportunity is selected 112 to ensure the desired angular coverage, and is generally larger than the angular data range to be selected for reconstruction from that window.

Figure 6A:
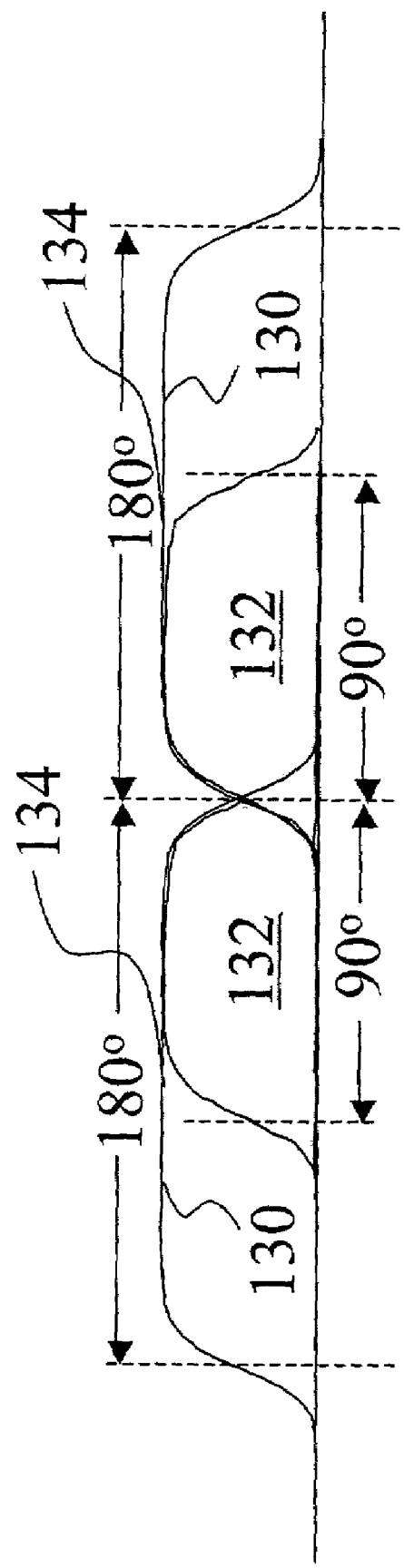
FIG. 6A shows a schematic representation of selection of data portions for reconstruction using cardiac segmented gating over two cardiac cycles where the two time windows are angularly adjacent.
Figure 6B:
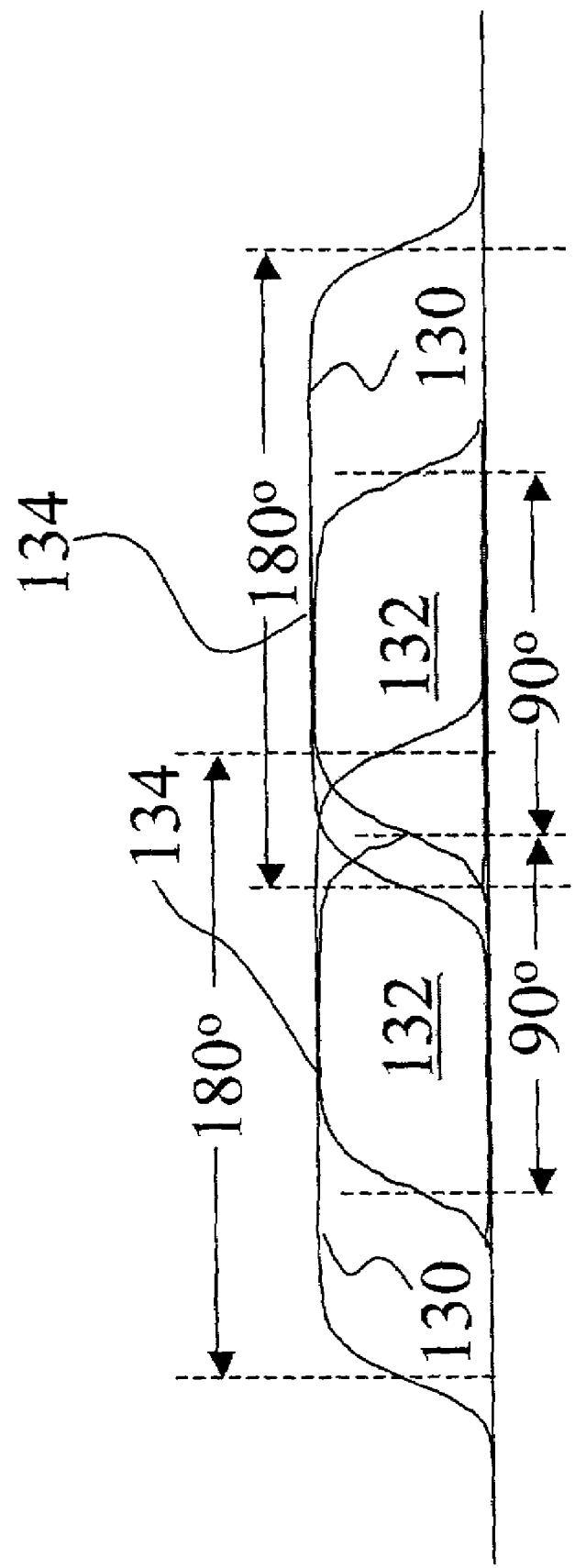
FIG. 6B shows a schematic representation of selection of data portions for reconstruction using cardiac segmented gating over two cardiac cycles where the two time windows include a partial angular overlap.

With reference to FIGS. 6A, 6B, and 6C, exemplary imaging using cardiac segmented gating over two cardiac cycles without the cardiac state concept, using a three-dimensional backprojection reconstruction technique requiring 180° coverage, is described. For this example, the number of cardiac cycles 106 equals two, and the selected cardiac state 110 occurs only once in each cardiac cycle. For a Feldkamp-type reconstruction, the selected data is weighted as is known to the art, such as using a cosine-weighting which spans 360° with a FWHM of 180° to define a window of opportunity which is 180° wide. The weighting provides a feathering of the data near the boundaries of the combined data set. FIG. 6A illustrates a "worst case" relationship between occurrences of the cardiac state 110 and the rotation of the gantry, in which the windows 130 have their centers 180° offset around the gantry. FIG. 6B represents a more common case in which the windows 130 are partially overlapping. FIG. 6C shows an optimal case in which the windows 130 are 90° apart, so that the selected is optimally positioned within the windows of opportunity.

With continuing reference to FIGS. 5, 6A, 6B, and 6C, in a step 114 data segment selections 132 are adaptively adjusted within the windows of opportunity 130 to optimally cover the desired angular range. For two windows 130 each having a center 134 corresponding to occurrences in successive cardiac cycles of a selected cardiac state, each window 130 has an effective width of 180°. Data segment selections 132 are adaptively adjusted 114 within the windows 130 to provide 180° plus fan contiguous angular coverage while keeping each selected data set 132 as close as possible to the selected cardiac state, i.e. to the center 134 of the window 130. The adaptively adjusted data sets 132 are combined to provide the selected 180° coverage. The combined data are reconstructed 116 to generate an image reconstruction.

In a suitable embodiment of the adaptive adjusting 114, the selected data segment selections 132 are adaptively adjusted using a constrained optimization in which the constraints include retaining each angular interval 132 within its associated time window 130 and the optimizing criteria include minimizing a separation between a center of each angular interval 132 and the center 134 of its associated time window 130. The adaptive adjusting 114 arranges the angular data segments 132 to collectively span at least the 180° plus fan contiguous angular coverage desired for optimal reconstructing 116.

It will be appreciated that because the windows of opportunity are selected with effective widths of 180°, even for a worst-case scenario in which the two windows precisely overlap (corresponding to a cardiac cycle period $T_{cc}$ being an integer multiple of the gantry rotation period $T_{rot}$, i.e. $T_{cc}=nT_{rot}$) the adaptive adjusting 114 provides 180° contiguous angular coverage, albeit with the selected data segments shifted 90° away from being centered on the occurrence of the selected cardiac state. Similarly, in the second limiting case (shown in FIG. 6A), wherein $T_{cc}=(n+\frac{1}{2})T_{rot}$, the selected 180° wide windows will be non-overlappingly contiguous and so a 90° shifting of the selected data segments results in angular continuity and full 180° angular coverage of the combined data segments. In less extreme cases (e.g., FIG. 6B or FIG. 6C), the method 100 adaptively adjusts the angular data segment selections within the windows of opportunity to provide the 180° angular coverage with minimal shift of the data segments away from the selected cardiac state.

With reference to FIG. 7, the technique 100 is amenable to assembling the 180° data set from three 60° data segments 142 selected from windows 140 in three successive cardiac cycles in which each window is centered on an occurrence of a selected cardiac state. Once again, the data segments 142 are adaptively selected to stay optimally close to centers 144 of the windows 140, which centers 144 correspond to occurrences of the selected cardiac state.

The same principle holds for data collected over a larger number of cardiac cycles. However, it will be recognized that as the number of cardiac cycles over which the data is collected increases, temporal resolution is improved but other artifacts can arise due to patient motion or drift in the cardiac cycle. In cone-beam CT, increasing the number of cardiac cycles over which the data is collected also increases the number of data segment boundaries. Each data segment boundary presents a potential inconsistency in the cone angle in the Z-direction in the combined complete data set. Such cone angle inconsistencies can produce image artifacts.

With continuing reference to FIGS. 1 and 5, in one suitable embodiment the reconstructed CT images are used to iteratively improve the cardiac state identification. Images are reconstructed according to the steps 102, 108, 112, 114, 116 using data segments selected from windows of opportunity each centered at a temporal position estimated to correspond to the selected cardiac state. For example, the ECG 24 can be used along with the cardiac state analyzer 40 to estimate a cardiac phase corresponding to the selected cardiac state. The window is in the first instance centered on the corresponding cardiac phase as identified by the ECG 24.

The reconstructed images are analyzed to more precisely estimate the temporal evolution of the cardiac state during the image data acquisition. The cardiac state identification is updated in a step 118 based on the updated information, and the reconstructing steps 108, 112, 114, 116 are repeated with updated windows of opportunity centered on improved estimates of temporal occurrences of the selected cardiac state 110 to provide improved images. The improvement of the estimates of temporal occurrences of the selected cardiac state 110 can be iteratively repeated to optimize the selection of data for the image reconstruction.

Figure 8:
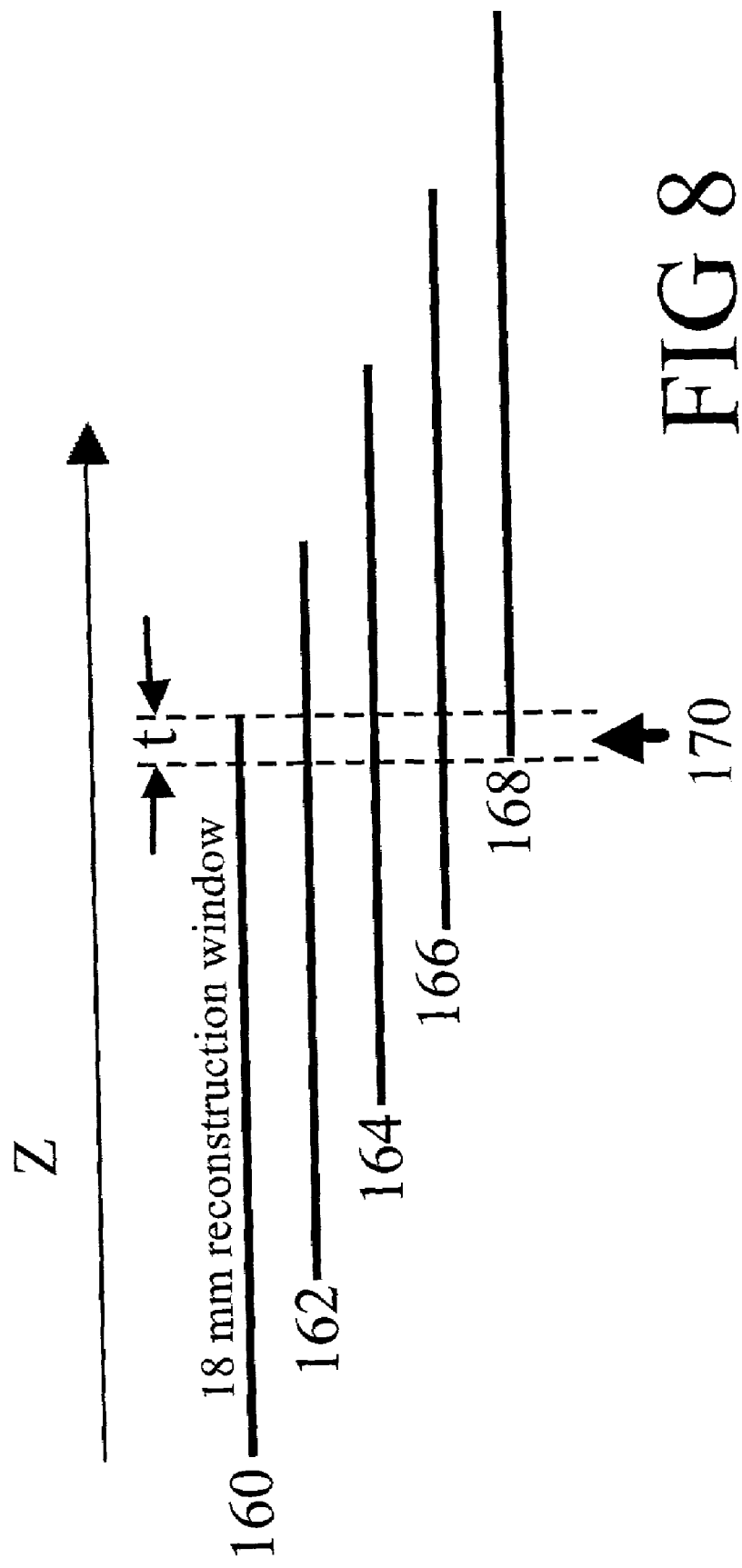
FIG. 8 shows a schematic representation of the position of a reconstruction window over five helical x-ray source rotations.
Figure 9:
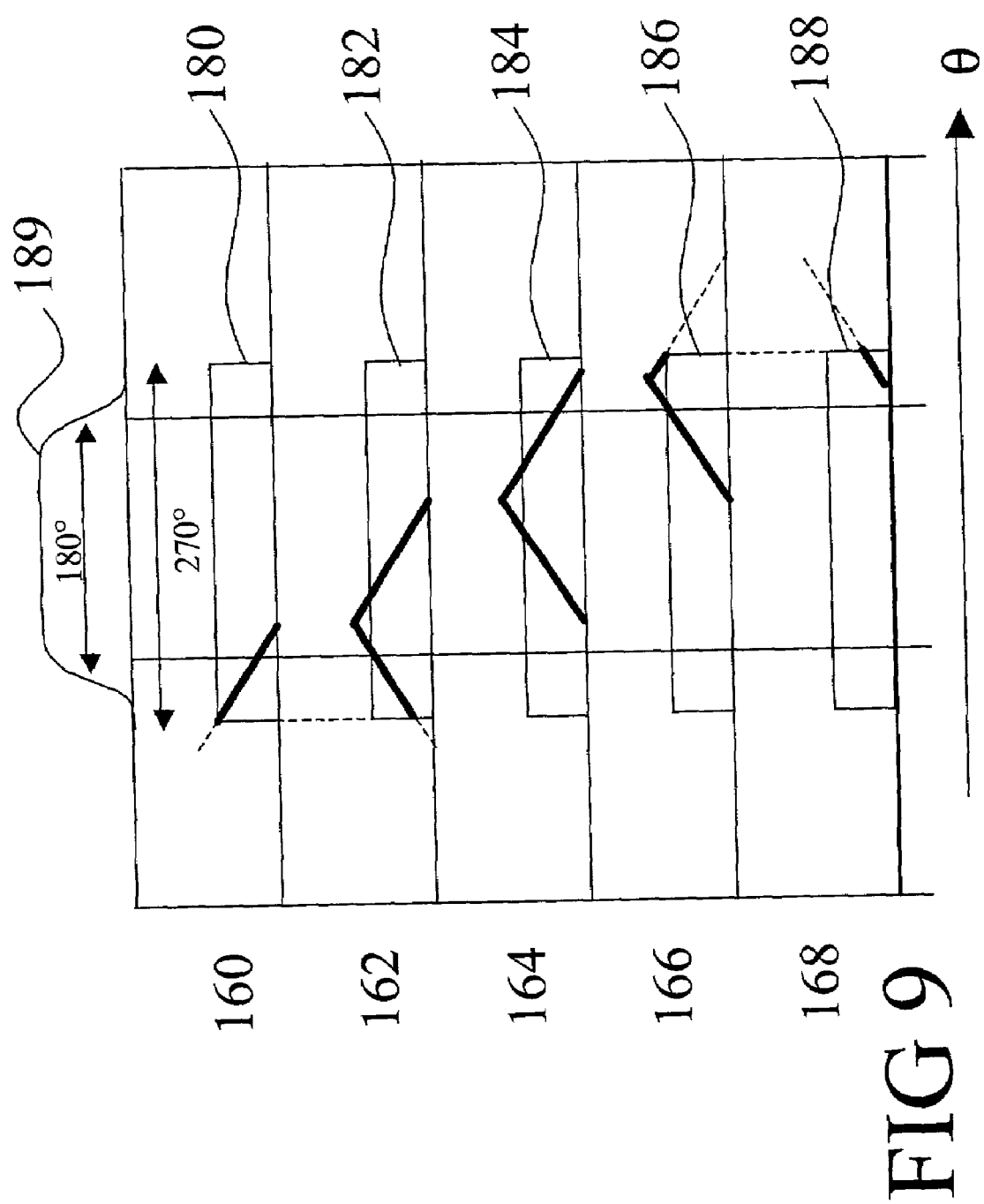
FIG. 9 shows a schematic representation of selection of five adaptive volume segments using cardiac segmented gating over five cardiac cycles, for a worst-case where the heart pulse rate equals the gantry rotation rate.
Figure 10:
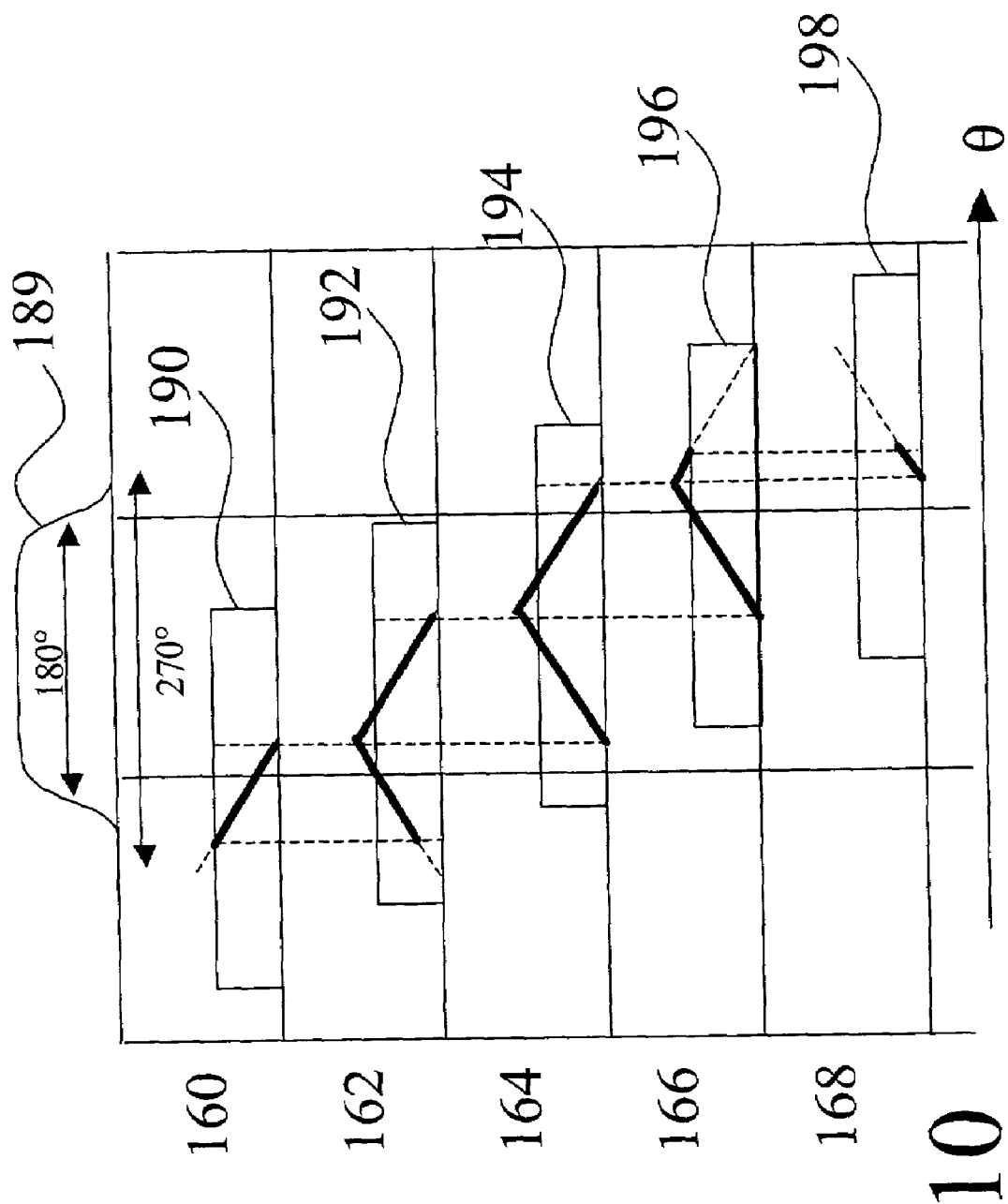
FIG. 10 shows a schematic representation of selection of five adaptive volume segments using cardiac segmented gating over five cardiac cycles, for a more usual case where the heart pulse rate substantially differs from the gantry rotation rate.

With reference to FIGS. 8–10, a more complex exemplary adaptive volume segmenting is described, in which the source is rotating at 120 rpm and adaptive volume segments are extracted from five source rotations. FIG. 8 shows the position of an 18 mm reconstruction window at five successive helical rotation periods 160, 162, 164, 166, 168 of the x-ray source. A slice 170 of thickness t remains within the reconstruction window over the five successive helical rotation periods 160, 162, 164, 166, 168, and so data from the five successive source rotations is available to reconstruct the slice 170.

FIG. 9 shows a worst-case scenario in which the patient's pulse equals the source rotation rate, i.e. 120 beats per minute. Because the x-ray source rotation rate equals the heart pulse rate, windows of opportunity 180, 182, 184, 186, 188 extend over the same angular (θ) range for all five helical rotation periods 160, 162, 164, 166, 168.

Also shown in FIG. 9 is a suitable weighting function 189 which is applied to the combined complete data set for the three-dimensional backprojection reconstruction. The weighting function 189 is a cosinusoidal weighting function with a FWHM of 180° and a total width of 270°. Each window of opportunity 180, 182, 184, 186, 188 extends over 270° so that even in the worst case scenario of FIG. 9 a complete set of data can be selected for reconstruction. It will be appreciated that a complete set of data for reconstruction in this case extends over 270°, with the weighting function 189 applied to reduce the contribution of data from the angular extremes to provide smoothing. Although a cosinusoidal weighting function is shown, other suitable weighting functions can instead be employed, such as a trapezoidal weighting function.

An adaptive volume segment with a triangular weighting covering a 90° full-width-at-half-maximum (FWHM) is used in selecting the data. By arranging the adaptive volume segments at 90° separations, each volume segment portion overlaps with one other volume segment portion, such that the five volume segments give full coverage over a 360° angular range. In FIG. 9, selected data within an adaptive volume segment is shown as a heavy continuous line, while portions of the volume segment that are not selected because they are outside of the windows of opportunity are shown as a light broken line. As seen in FIG. 9, the coincidence of the heart pulse rate and the gantry rotation rate results in four of the five volume segments extending to an edge of windows of opportunity 160, 162, 166, and 168.

FIG. 10 shows a more usual case in which the heart pulse rate differs from the gantry rotation rate. In FIG. 10, the gantry rotation remains at 120 rpm while the heart pulse rate is decreased to about 100 beats per minute. As a result, windows of opportunity 190, 192, 194, 196, 198 are not angularly coextensive, and in each case the adaptive volume segment is selected to remain well within the window of opportunity. This corresponds to reduced motion blurring in the reconstructed image.

Figure 11A:
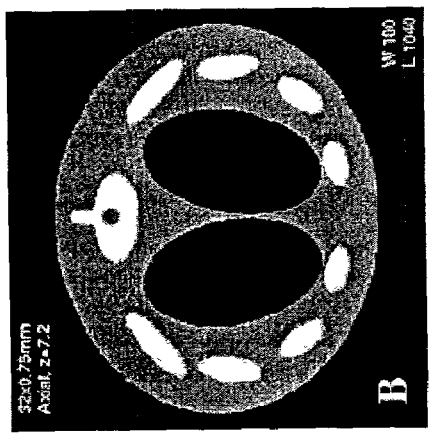
FIG. 11A shows an exemplary image of a phantom located 14.5 mm off-axis, the image obtained using a cone-beam CT system and method embodying the invention, a 64×0.75 mm axial slice and a cosine-weighted 360° Feldkamp reconstruction.

With reference to FIGS. 11A–11D, the effect of Z-direction cone angle inconsistencies at segment boundaries is illustrated using exemplary off-axis imaging of a three-dimensional phantom using axial cardiac scanning (i.e., zero helical pitch) and the method 100 of FIG. 5. The 'ribs' of the phantom are oriented in three-dimensions to provide a severe test of cone-beam image quality. FIG. 11A illustrates image quality for a large (64×0.75 mm slice) array obtained in a 14.5 mm off-axis position using a cosine-weighted 360° Feldkamp reconstruction wherein the cosine weighting spans 360° with a FWHM of 180°. It will be observed that there are some artifacts at the edges of the ribs; however, the overall image quality is good. The artifacts result from the cone angle inconsistency in the Z-direction at the boundaries of the single data segment.

Figure 11B:
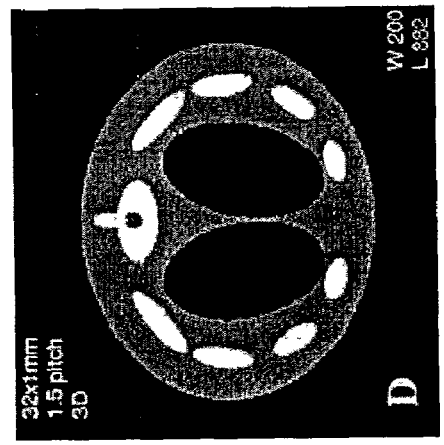
FIG. 11B shows an exemplary image of a phantom located 7.2 mm off-axis and the cone-beam angle scaled down by 50% versus the imaging of FIG. 11A, the image obtained using a cone-beam CT system and method embodying the invention, a 32×0.75 mm axial slice and a cosine-weighted 360° Feldkamp reconstruction.

The image quality improves in FIG. 11B which shows an image for the same imaging parameters, a reduced off-axis position of 7.2 mm, and a corresponding 50% reduction in the cone-beam angle. The image quality here is significantly improved versus the image of FIG. 11A, because the cone angle inconsistency at the boundaries of the single data segment is reduced.

Figure 11C:
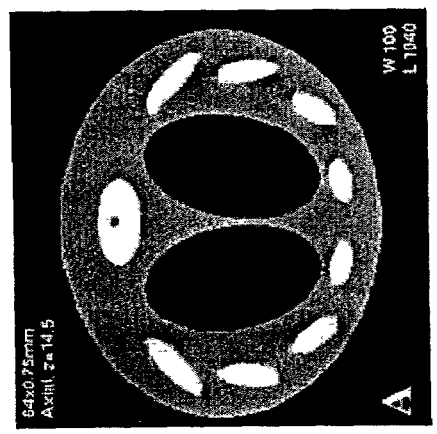
FIG. 11C shows an exemplary prior art image of a phantom acquired using a 4-slice (multi-slice) CT system and spiral scanning method.

With continuing reference to FIGS. 11A–11D, for comparison FIG. 11C shows a conventional prior art multi-slice image of the phantom. This image is representative of typical image quality presently obtained. Comparison with FIG. 11A shows that the image artifacts introduced by a relatively large cone angle inconsistency is comparable to the level of artifacts observed using present imaging techniques. The image of FIG. 11C provides a standard by which to judge adequacy of image quality for clinical scans.

Figure 11D:
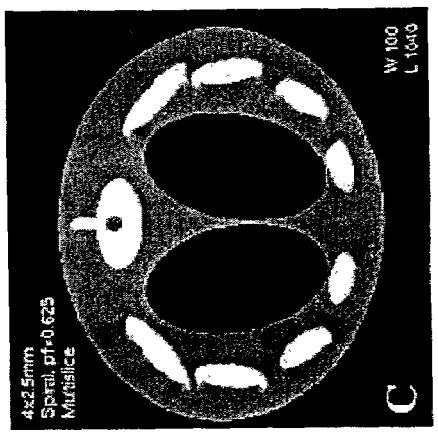
FIG. 11D shows an exemplary prior art image of a phantom obtained using large-pitch cone-beam CT imaging that eliminates discontinuities in the cone angle.

FIG. 11D shows a helical cone-beam scan using a large pitch such that the cone angle inconsistency at the boundaries of the data segment are eliminated. Comparison with FIG. 11B shows the artifacts introduced in the case of a moderate cone-angle are minimal. It will be appreciated that a large helical pitch such as is used in acquiring the image of FIG. 11 is typically incompatible with cardiac imaging, because the large pitch substantially reduces the time that a cardiac slice remains in the field of view. This in turn reduces the number of cardiac cycles over which data can be acquired when using a large helical pitch.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for acquiring diagnostic imaging data of a dynamically moving organ, the method comprising:
   monitoring positional state of the organ motion as a function of time by measuring a physiological parameter and applying a positional state relationship that relates positional state to the measured physiological parameter;
   identifying at least two occurrences of a selected positional state within each cycle of motion of the dynamically moving organ based on the measured physiological parameter and the state relationship;
   selecting time windows arranged about identified occurrences of the selected positional state including at least said identified at least two occurrences;
   acquiring imaging data of the dynamically moving organ at least during the time windows;
   combining portions of the imaging data acquired during the time windows corresponding to the selected positional state to form an image data set; and
   reconstructing an image representation of the moving organ in the selected positional state from the image data set.

2. The imaging method as set forth in claim 1, further including:
   defining a parametric functional model of the positional state relationship, the parametric functional model being used in relating the positional state to the measured physiological parameter.

3. The imaging method as set forth in claim 1, wherein the positional state includes a volume of a selected heart chamber, and the measuring of a physiological parameter includes:
   performing an electrocardiographic measurement.

4. The method as set forth in claim 1, wherein the combining step includes:
   selecting a data portion within each window such that the data portions provide a selected angular coverage.

5. The method as set forth in claim 1, wherein the positional state includes one of a spatial position of the organ and a spatial volume of the organ.

6. The method as set forth in claim 1, wherein the dynamically moving organ includes at least a portion of the heart, and the time windows include:
   a first time window arranged about a first occurrence of the selected positional state during the systolic cardiac cycle portion; and
   a second time window arranged about a second occurrence of the selected positional state during the diastolic cardiac cycle portion.

7. A computer medium programmed to implement the method of claim 1.

8. An imaging method for acquiring diagnostic imaging data of a dynamically moving organ, the method comprising:
   monitoring positional states of the moving organ as a function of time;
   selecting time windows arranged about occurrences of a selected positional state;
   acquiring imaging data of the dynamically moving organ at least during the time windows using an orbiting x-ray source;
   for each time window, selecting an angular segment of the orbiting x-ray source substantially centered within the time window;
   shifting each angular segment within its corresponding time window to provide a complete image data set for reconstruction while optimizing centering of the angular segments within their respective windows; and
   reconstructing an image representation of the moving organ in the selected positional state from the complete image data set.

9. The imaging method as set forth in claim 8, further including:
   correcting the occurrences of the selected positional state based on the reconstructed image representations;
   adjusting the arrangement of the time windows based on the corrected occurrences; and
   repeating the combining and reconstructing steps using the adjusted time windows.

10. The method as set forth in claim 8, wherein the time windows include two time windows within a single cycle of the dynamically moving organ.

11. The method as set forth in claim 8, wherein the time windows include time windows arranged in at least two consecutive cycles of the dynamically moving organ.

12. The method as set forth in claim 8, wherein the acquiring of imaging data includes:
   acquiring cone-beam computed tomography (CT) imaging data using a generally helically orbiting x-ray source.

13. The method as set forth in claim 8, wherein the complete image data set includes data spanning 180° of angular orientations of the cone-beam plus at least a fan angle.

14. The method as set forth in claim 8, wherein the complete image data set comprises at least two angularly contiguous and temporally discontinuous angular segments.

15. The method as set forth in claim 8, further including:
   weighting each angular segment.

16. The method as set forth in claim 8, wherein the reconstructing step includes:
   weighting the complete image data set by a weighting function that reduces the contribution of data from the angular extremities; and
   performing a three-dimensional backprojection to generate the image representation.

17. A computer medium programmed to implement the method of claim 8.

18. An apparatus for computed tomography (CT) imagine of a cyclically moving organ, the apparatus compnsing:
   a positional state monitor that monitors a positional state of the cyclically moving organ;
   a cone-beam CT scanner that acciuires image data at least within a plurality of time windows, each time window centered about an occurrence of a selected positional state of the organ;
   a means for selecting a data segment of the acciuired image data in each time window, which data segments (1) taken together form a complete set of image data for reconstruction, and (2) are optimally centered within the time windows; and
   a reconstruction processor that reconstructs the selected data segments into an image representation of the moving organ in the selected positional state.

19. The apparatus as set forth in claim 18, wherein the cyclically moving organ is a cardiac organ, and the positional state monitor includes:
   an electrocardiograph that monitors a cardiac phase; and
   a cardiac state analyzer that relates the measured cardiac phase with a positional cardiac state.

20. The apparatus as set forth in claim 18, wherein the positional state monitor includes:
   an auxiliary imaging apparatus that images a position of the cyclically moving organ during the CT image data acquisition.

21. The apparatus as set forth in claim 20, wherein the auxiliary imaging apparatus includes an ultrasonic imaging apparatus.

22. An apparatus for acquiring volumetric medical imaging data of a dynamically moving organ, the apparatus comprising:
   a means for monitoring an anatomical state of the organ motion cycling;
   a means for determining time windows centered on occurrences of substantially similar states of organ motion cycle at different phases of the organ motion;
   a means for acquiring imaging data at least during the time windows;
   a means for combining portions of the imaging data acquired during the time windows to form a complete image data set; and
   a means for reconstructing an image representation from the complete image data set.

23. The apparatus as set forth in claim 22, wherein the acquiring means includes:
   a means for projecting x-rays into an examination region containing the dynamically moving organ;
   a means for detecting x-ray intensity after passing through the examination region;
   a means for assembling the detected x-ray intensity data to form computed tomography projection data;
   a means for rotating the means for projecting to acquire projection data at a plurality of projection angles; and
   a means for advancing the dynamically moving organ linearly in a direction transverse to the rotation plane.

24. The apparatus as set forth in claim 22, wherein the combining means includes:
   a means for selecting an angular interval within each time window;
   a means for adaptively adjusting each angular interval using a constrained optimization in which the constraints include retaining each angular interval within its associated time window and the optimizing criteria include minimizing a separation between a center of each angular interval and the center of its associated time window, the adaptive adjusting arranging the angular intervals to collectively span at least an angular range corresponding to an angular range of a complete data set; and
   a means for combining projection data portions corresponding to the adaptively adjusted angular intervals to form the complete image data set.

25. The apparatus as set forth in claim 22, wherein the means for monitoring a state include:
   a means for monitoring a temporal percentage phase of a cycle of the dynamically moving organ; and
   a means for correlating the temporal percentage phase with an anatomical state of at least a portion of the dynamically moving organ.

* * * * *